(12) United States Patent
McMillian et al.

(10) Patent No.: US 6,586,584 B2
(45) Date of Patent: Jul. 1, 2003

(54) SEQUENCES AND METHODS FOR DETECTION OF HEPATITIS C VIRUS

(75) Inventors: Ray A. McMillian, Timonium, MD (US); Tobin J. Hellyer, Owings Mills, MD (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 09/770,158

(22) Filed: Jan. 29, 2001

(65) Prior Publication Data

US 2003/0032004 A1 Feb. 13, 2003

(51) Int. Cl.[7] .................. C07N 21/00; C12P 15/51; C12P 39/00; C12N 15/09; C12N 15/33
(52) U.S. Cl. ............... 536/24.3; 536/24.2; 536/24.33; 435/5; 435/6; 435/69.1; 435/91.2; 435/91.21; 435/450
(58) Field of Search ................. 435/5, 6, 450, 435/91.2, 91.21, 69.1; 536/24.2, 24.3, 24.33

(56) References Cited

U.S. PATENT DOCUMENTS

| | | |
|---|---|---|
| 5,372,928 A | 12/1994 | Miyamura et al. |
| 5,427,909 A | 6/1995 | Okamoto et al. |
| 5,428,145 A | 6/1995 | Okamoto et al. |
| 5,527,669 A | 6/1996 | Resnick et al. |
| 5,550,016 A | 8/1996 | Okamoto |
| 5,580,718 A | 12/1996 | Resnick et al. |
| 5,620,843 A | 4/1997 | Hellings et al. |
| 5,712,088 A | 1/1998 | Houghton et al. |
| 5,714,596 A | 2/1998 | Houghton et al. |
| 5,837,442 A | 11/1998 | Tsang |
| 5,847,101 A | 12/1998 | Okayama et al. |
| 5,856,458 A | 1/1999 | Okamoto et al. |
| 5,863,719 A | 1/1999 | Houghton et al. |

FOREIGN PATENT DOCUMENTS

| | | |
|---|---|---|
| EP | 0 377 303 B1 | 12/1989 |
| EP | 0 551 275 B1 | 6/1991 |
| EP | 0 543 924 B1 | 8/1991 |
| EP | 0 510 952 A1 | 4/1992 |
| EP | 0 529 493 B1 | 8/1992 |
| EP | 0 787 807 A2 | 8/1992 |
| EP | 0 531 974 A1 | 9/1992 |
| EP | 0 532 258 A2 | 9/1992 |
| EP | 0 633 320 A1 | 11/1993 |
| EP | 0 633 321 A1 | 6/1994 |
| EP | 0 776 981 A2 | 11/1996 |
| WO | WO 90/14436 | 11/1990 |
| WO | WO 92/19743 | 11/1992 |
| WO | WO 94/12670 | 6/1994 |
| WO | WO 9603528 A2 | 2/1996 |
| WO | WO 96/39500 | 12/1996 |
| WO | WO 97/40190 | 10/1997 |

OTHER PUBLICATIONS

Ausubel et al. Short Protocols in Molecular Biology 1999, Fourth edition, Edited by Ausubel et al. Published by John Wiley & Sons, Inc. pp. 6–6 to 6–8.*
Bains W. (Molecular Biology and Technology 1995, Edited by Meyers et al. pp. 441–443.*
X. Forns et al., Methods for Determining the Hepatitis C Virus Genotype, Viral Hepatitis, 1998, vol. 4, No. 1, 1–19.
The Scientific Challenge of Hepatitis C, Science, Jul. 2, 1999, vol. 285, p. 26.
J. Mellor, Genotype Dependence of Hepatitic C Virus Load Measurement in Commerically Available Quantitative Assays, J. of Clinical Microbiology, Aug. 1999, p. 2525–2532.
F. McOmish et al., Geographical Distribution of Hepatitis C Virus Genotypes in Blood Donor: an International Collaborative Survey, J of Clinical Microbiology, Apr. 1994, p 884–892.
J. Bukh, Sequence Analysis of the Core Gene of 14 Hepatitis C Virus Genotypes, Proc. Natl. Acad. Sci. USA, vol. 91, p 8239–8243, Aug. 1994.
J. Bukh, Sequence Analysis of the 5' Noncoding Region of Hepatitis C Virus, Proc. Natl. Acad. Sci. USA, vol. 89, p 4942–4946.

* cited by examiner

*Primary Examiner*—James Housel
*Assistant Examiner*—B Q Li
(74) *Attorney, Agent, or Firm*—Allan M. Kiang

(57) ABSTRACT

Primers and probes derived from the 5' untranslated region of the HCV genome which facilitate detection and/or quantification of all presently known genotypes of HCV. Disclosed sequences may be used in a variety of primer and probe constructs for amplification and/or detection of HCV nucleic acids.

15 Claims, No Drawings

SEQUENCE LISTING

<160> NUMBER OF SEQ ID NOS: 35

<210> SEQ ID NO 1
<211> LENGTH: 37
<212> TYPE: DNA
<213> ORGANISM: Hepatitis C virus

<400> SEQUENCE: 1
cgattcgcct ccagacttct cgggtggtct gcggaac         37

<210> SEQ ID NO 2
<211> LENGTH: 38
<212> TYPE: DNA
<213> ORGANISM: Hepatitis C virus

<400> SEQUENCE: 2
cgattcgcct ccagacttct cgggatggtc tgcggaac                    38

<210> SEQ ID NO 3
<211> LENGTH: 37
<212> TYPE: DNA
<213> ORGANISM: Hepatitis C virus

<400> SEQUENCE: 3
accgcatcga atgactgtct cggggaaagg acccggt                     37

<210> SEQ ID NO 4
<211> LENGTH: 38
<212> TYPE: DNA
<213> ORGANISM: Hepatitis C virus

<400> SEQUENCE: 4
actcgcatcg aatgactgtc tcggggaaag gacccggt                    38

<210> SEQ ID NO 5
<211> LENGTH: 37
<212> TYPE: DNA
<213> ORGANISM: Hepatitis C virus

<400> SEQUENCE: 5
accgcatcga atgactgtct cggggaaagg acccagt                     37

<210> SEQ ID NO 6
<211> LENGTH: 38
<212> TYPE: DNA
<213> ORGANISM: Hepatitis C virus

<400> SEQUENCE: 6
actcgcatcg aatgactgtc tcggggaaag gacccagt                    38

<210> SEQ ID NO 7
<211> LENGTH: 38
<212> TYPE: DNA
<213> ORGANISM: Hepatitis C virus

<400> SEQUENCE: 7
accgcatcga atgactgtct cggggaaagg accctgtc                    38

<210> SEQ ID NO 8
<211> LENGTH: 39
<212> TYPE: DNA
<213> ORGANISM: Hepatitis C virus

<400> SEQUENCE: 8
actcgcatcg aatgactgtc tcggggaaag gaccctgtc                   39

<210> SEQ ID NO 9
<211> LENGTH: 39
<212> TYPE: DNA
<213> ORGANISM: Hepatitis C virus

<400> SEQUENCE: 9
cgattccgct ccagacttct cgggtgggta gcgaaaggc                   39

<210> SEQ ID NO 10
<211> LENGTH: 38
<212> TYPE: DNA
<213> ORGANISM: Hepatitis C virus

<400> SEQUENCE: 10
cgattccgct ccagacttct cgggtgggta gcgaaagg          38

<210> SEQ ID NO 11
<211> LENGTH: 38
<212> TYPE: DNA
<213> ORGANISM: Hepatitis C virus

<400> SEQUENCE: 11
cgattccgct ccagacttct cggggggtag cgaaaggc          38

<210> SEQ ID NO 12
<211> LENGTH: 37
<212> TYPE: DNA
<213> ORGANISM: Hepatitis C virus

<400> SEQUENCE: 12
accgcatcga atgcatgtct cgggctcctg gggcact          37

<210> SEQ ID NO 13
<211> LENGTH: 38
<212> TYPE: DNA
<213> ORGANISM: Hepatitis C virus

<400> SEQUENCE: 13
accgcatcga atgcatgtct cgggcctcct ggggcact          38

<210> SEQ ID NO 14
<211> LENGTH: 37
<212> TYPE: DNA
<213> ORGANISM: Hepatitis C virus

<400> SEQUENCE: 14
accgcatcga atgcatgtct cgggcctcct ggggcac          37

<210> SEQ ID NO 15
<211> LENGTH: 37
<212> TYPE: DNA
<213> ORGANISM: Hepatitis C virus

<400> SEQUENCE: 15
accgcatcga atgcatgtct cggggggcact cgcaagc          37

<210> SEQ ID NO 16
<211> LENGTH: 29
<212> TYPE: DNA
<213> ORGANISM: Hepatitis C virus

<400> SEQUENCE: 16
tagcacccga gtgctccggt gtactcacc          29

<210> SEQ ID NO 17
<211> LENGTH: 29
<212> TYPE: DNA
<213> ORGANISM: Hepatitis C virus

<400> SEQUENCE: 17
tagcacccga gtgctacgga accggtgag          29

<210> SEQ ID NO 18
<211> LENGTH: 28
<212> TYPE: DNA
<213> ORGANISM: Hepatitis C virus

<400> SEQUENCE: 18
tagcacccga gtgctgcgga accggtga 28

<210> SEQ ID NO 19
<211> LENGTH: 28
<212> TYPE: DNA
<213> ORGANISM: Hepatitis C virus

<400> SEQUENCE: 19
tagcacccga gtgcttgcgg aaccggtg 28

<210> SEQ ID NO 20
<211> LENGTH: 33
<212> TYPE: DNA
<213> ORGANISM: Hepatitis C virus

<400> SEQUENCE: 20
tagcacccga gtgctgcctg ataggttgct tgc 33

<210> SEQ ID NO 21
<211> LENGTH: 33
<212> TYPE: DNA
<213> ORGANISM: Hepatitis C virus

<400> SEQUENCE: 21
tagcacccga gtgctgcctg atagggagct tgc 33

<210> SEQ ID NO 22
<211> LENGTH: 34
<212> TYPE: DNA
<213> ORGANISM: Hepatitis C virus

<400> SEQUENCE: 22
tagcacccga gtgcttgcct gatagggagc ttgc 34

<210> SEQ ID NO 23
<211> LENGTH: 33
<212> TYPE: DNA
<213> ORGANISM: Hepatitis C virus

<400> SEQUENCE: 23
tagcacccga gtgctgcaag ctccctatca ggc 33

<210> SEQ ID NO 24
<211> LENGTH: 34
<212> TYPE: DNA
<213> ORGANISM: Hepatitis C virus

<400> SEQUENCE: 24
tagcacccga gtgctgcaag ctccctatca ggca 34

<210> SEQ ID NO 25
<211> LENGTH: 34
<212> TYPE: DNA
<213> ORGANISM: Hepatitis C virus

<400> SEQUENCE: 25

-continued tagcacccga gtgctcgcaa gctccctatc aggc                              34

<210> SEQ ID NO 26
<211> LENGTH: 35
<212> TYPE: DNA
<213> ORGANISM: Hepatitis C virus

<400> SEQUENCE: 26
tagcacccga gtgctcgcaa gctccctatc aggca                             35

<210> SEQ ID NO 27
<211> LENGTH: 34
<212> TYPE: DNA
<213> ORGANISM: Hepatitis C virus

<400> SEQUENCE: 27
tagcacccga gtgctgcgaa agtccttgtg gtac                              34

<210> SEQ ID NO 28
<211> LENGTH: 35
<212> TYPE: DNA
<213> ORGANISM: Hepatitis C virus

<400> SEQUENCE: 28
tagcacccga gtgcttagcg aaagtccttg tggta                             35

<210> SEQ ID NO 29
<211> LENGTH: 36
<212> TYPE: DNA
<213> ORGANISM: Hepatitis C virus

<400> SEQUENCE: 29
tagcacccga gtgctgtagc gaaagtcctt gtggta                            36

<210> SEQ ID NO 30
<211> LENGTH: 35
<212> TYPE: DNA
<213> ORGANISM: Hepatitis C virus

<400> SEQUENCE: 30
tagcacccga gtgctgtagc gaaagtcctt gtggt                             35

<210> SEQ ID NO 31
<211> LENGTH: 13
<212> TYPE: DNA
<213> ORGANISM: Hepatitis C virus

<400> SEQUENCE: 31
ccctcccgtg aga                                                     13

<210> SEQ ID NO 32
<211> LENGTH: 13
<212> TYPE: DNA
<213> ORGANISM: Hepatitis C virus

<400> SEQUENCE: 32
cctcccgtga gag                                                     13

<210> SEQ ID NO 33
<211> LENGTH: 13
<212> TYPE: DNA
<213> ORGANISM: Hepatitis C virus

<400> SEQUENCE: 33

-continued

```
gtcttgcggg ggc                                                  13

<210> SEQ ID NO 34
<211> LENGTH: 16
<212> TYPE: DNA
<213> ORGANISM: Hepatitis C virus

<400> SEQUENCE: 34
gcgtgctccc gctaga                                               16

<210> SEQ ID NO 35
<211> LENGTH: 13
<212> TYPE: DNA
<213> ORGANISM: Hepatitis C virus

<400> SEQUENCE: 35
gcacggtcta cga                                                  13
```

US 6,586,584 B2

SEQUENCES AND METHODS FOR DETECTION OF HEPATITIS C VIRUS

FIELD OF THE INVENTION

The present invention relates to materials and methods for detection of Hepatitis C viral nucleic acids, in particular to probes and primers for detection of Hepatitis C in hybridization and amplification assays.

BACKGROUND OF THE INVENTION

Hepatitis C virus (HCV) is a member of the virus family Flaviviridae and infects at least 1% of the world's population. Infected individuals are at increased risk to develop cirrhosis of the liver and hepatocellular carcinoma. The viral genome is a single strand of RNA which contains a single gene. The polyprotein which is expressed is subsequently processed into at least ten functional proteins. The genome of HCV is highly heterogeneous and has an estimated mutation rate of about $10^{-2}$ per base per generation. At least 100 strains have been identified and grouped into six major genotypes.

At the present time there is no reliable method for growth of HCV in vitro, which makes immunological methods of detection difficult to perform and the results unreliable. Quantitation of viral RNA in plasma is used extensively as a prognostic marker for patients undergoing treatment and as a means for monitoring their response to therapy. Due to the genomic heterogeneity, however, existing molecular assays for detection of HCV RNA are limited by their inability to detect all genotypes with equal efficiency. The probes and primers of the present invention may provide rapid and sensitive detection of HCV nucleic acids and offer an attractive alternative to immunological assays.

SUMMARY OF THE INVENTION

The present invention provides primers and probes derived from the 5' untranslated region of the HCV genome which are predicted to facilitate detection and/or quantification of all presently known genotypes of HCV (1–6). That is, a single amplification primer pair according to the invention should efficiently amplify all known genotypes of HCV, which may then be detected in a single detection step using the detector probes and primers of the invention.

DETAILED DESCRIPTION OF THE INVENTION

The primers, hybridization probes and detector primers of the present invention are based on portions of the 5' untranslated region (UTR) of the HCV genome. Initially, design of the disclosed primers and probes was based on relatively conserved regions in an alignment of multiple HCV sequences. One goal was to develop probes and primers which, in spite of heterogeneity in the sequence, would be expected to provide amplification, detection and/or quantitation of all presently known HCV genotypes with approximately equal efficiency. In some cases this was accomplished by overlapping the hybridization site of the 5' ends of certain of the detector probes with the hybridization site of the 3' end an amplification primer. This approach took advantage of short stretches of relative sequence conservation in the primer hybridization region and avoided much of the sequence heterogeneity evident in the intervening region between the two amplification primers. This technique also allowed use of a smaller target sequence, thereby improving amplification efficiency.

As used herein, an amplification primer is an oligonucleotide for amplification of a target sequence by extension of the oligonucleotide after hybridization to the target sequence or by ligation of multiple oligonucleotides which are adjacent when hybridized to the target sequence. At least a portion of the amplification primer hybridizes to the target. This portion is referred to as the target binding sequence and it determines the target-specificity of the primer. In addition to the target binding sequence, certain amplification methods require specialized non-target binding sequences in the amplification primer. These specialized sequences are necessary for the amplification reaction to proceed and typically serve to append the specialized sequence to the target. For example, the amplification primers used in SDA (Strand Displacement Amplification) include a restriction endonuclease recognition site 5' to the target binding sequence (U.S. Pat. Nos. 5,455,166 and 5,270,184). NASBA, (Nucleic Acid Sequence Based Amplification) 3SR (Self Sustaining Sequence Replication) and transcription based amplification primers require an RNA polymerase promoter linked to the target binding sequence of the primer. Linking such specialized sequences to a target binding sequence for use in a selected amplification reaction is routine in the art. In contrast, amplification methods such as PCR which do not require specialized sequences at the ends of the target, generally employ amplification primers consisting of only target binding sequence.

As used herein, the terms "primer" and "probe" refer to the function of the oligonucleotide. A primer is typically extended by polymerase or ligation following hybridization to the target but a probe typically is not. A hybridized oligonucleotide may function as a probe if it is used to capture or detect a target sequence, and the same oligonucleotide may function as a primer when it is employed as a target binding sequence in an amplification primer. It will therefore be appreciated that any of the target binding sequences disclosed herein for amplification, detection or quantitation of HCV may be used either as hybridization probes or as target binding sequences in primers for detection or amplification, optionally linked to a specialized sequence required by the selected amplification reaction or to facilitate detection.

Based on the alignment of the 5' untranslated regions of multiple HCV genotypes, the following amplification primers were designed for testing in SDA reactions. Target binding sequences are underlined. The remaining 5' portion of the sequence comprises the restriction endonuclease recognition site (RERS) that is required for the SDA reaction to proceed plus a generic non-target-specific tail sequence. It will be readily apparent that the target binding sequences may be used alone to amplify the target in reactions which do not require specialized sequences or structures (e.g., PCR) and that other specialized sequences required by amplification reactions other than SDA (e.g., an RNA polymerase promoter) may be substituted for the RERS-containing sequence shown below. "S1" and "S2" in the primer name indicates "right" and "left" primers, respectively, when the oligonucleotides are used in amplification reactions:

| AMPLIFICATION PRIMERS FOR HCV REGION 1 | | |
|---|---|---|
| 1S1.1 | CGATTCGCCTCCAGACTTCTCGGGTGGTCTGCGGAAC | SEQ ID NO:1 |
| 1S1.2 | CGATTCGCCTCCAGACTTCTCGGGATGGTCTGCGGAAC | SEQ ID NO:2 |
| 1S2.1 | ACCGCATCGAATGACTGTCTCGGGGAAAGGACCCGGT | SEQ ID NO:3 |
| 1S2.1a | ACTCGCATCGAATGACTGTCTCGGGGAAAGGACCCGGT | SEQ ID NO:4 |
| 1S2.2 | ACCGCATCGAATGACTGTCTCGGGGAAAGGACCCAGT | SEQ ID NO:5 |
| 1S2.2a | ACTCGCATCGAATGACTGTCTCGGGGAAAGGACCCAGT | SEQ ID NO:6 |
| 1S2.3 | ACCGCATCGAATGACTGTCTCGGGGAAAGGACCC(T)GTC | SEQ ID NO:7 |
| 1S2.3a | ACTCGCATCGAATGACTGTCTCGGGGAAAGGACCC(T)GTC | SEQ ID NO:8 |

| AMPLIFICATION PRIMERS FOR HCV REGION 3 | | |
|---|---|---|
| 3S1a.1 | CGATTCCGCTCCAGACTTCTCGGGTGGGT(A)GCGAAAGGC | SEQ ID NO:9 |
| 3S1b.1 | CGATTCCGCTCCAGACTTCTCGGGTGGGT(A)GCGAAAGG | SEQ ID NO:10 |
| 3S1c.1 | CGATTCCGCTCCAGACTTCTCGGGGGGT(A)GCGAAAGGC | SEQ ID NO:11 |
| 3S2a.1 | ACCGCATCGAATGCATGTCTCGGGCTCC(T)GGGGCACT | SEQ ID NO:12 |
| 3S2b.1 | ACCGCATCGAATGCATGTCTCGGGCCTCC(T)GGGGCACT | SEQ ID NO:13 |
| 3S2c.1 | ACCGCATCGAATGCATGTCTCGGGCCTCC(T)GGGGCAC | SEQ ID NO:14 |
| 3S2d.1 | ACCGCATCGAATGCATGTCTCGGGGGCACTCGCAAGC | SEQ ID NO:15 |

(X) = Deliberately mismatched bases

The following detector primers were also designed for detection of amplification products produced using the amplification primers. They hybridize to the target sequence downstream of amplification primers so that they are displaced during the amplification reaction. An advantage of this detection method is that the target sequence can be detected and/or quantified as the amplification reaction is occurring, i.e., in "real-time" rather than at an endpoint, as is known in the art. The target binding sequences of the primers are underlined. The remaining portion of the sequence forms a hairpin structure which is typically labeled to facilitate detection of amplification products, for example as described in U.S. Pat. No. 5,98,869. It will be readily apparent that the target sequence may be used alone for detection (typically linked to a detectable label) and that other detectable sequences and labels may be substituted for the hairpin as is known in the art (e.g., G-quartets, linear sequences for specific probe hybridization, or restriction sites). See, for example, U.S. Pat. Nos. 5,547,861; 5,928,869; 5,593,867; 5,550,025; 5,935,791; 5,888,739; 5,846,726.

SEQ ID NO:16 and SEQ ID NOs:20–26 are conventional non-overlapping detector primers which contain a hairpin as described in U.S. Pat. No. 5,928,869. SEQ ID NOs:17–19 and SEQ ID NOs:27–30 also contain the hairpin but the 5' end of the target binding sequences overlap with the 3' end of the target binding sequences of the upstream amplification primers. Bumper primers used in SDA were also designed. The entire sequence of these oligonucleotides consists of target binding sequence, and "B1" and "B2" in the primer name indicated "right" and "left" primers, respectively, when used in an amplification reaction:

| BUMPER PRIMERS FOR HCV REGION 1 | | |
|---|---|---|
| 1B1.1 | CCCTCCCGTGAGA | SEQ ID NO:31 |
| 1B1.2 | CCTCCCGTGAGAG | SEQ ID NO:32 |
| 1B2.1 | GTCTTGCGGGGGC | SEQ ID NO:33 |

| DETECTOR PRIMERS FOR HCV REGION 1 | | |
|---|---|---|
| 1DR1.1 | TAGCACCCGAGTGCTCCGGTGTACTCACC | SEQ ID NO:16 |
| 1DOL1.1 | TAGCACCCGAGTGCTACGGAACCGGTGAG | SEQ ID NO:17 |
| 1DOL2 | TAGCACCCGAGTGCTGCGGAACCGGTGA | SEQ ID NO:18 |
| 1DOL3 | TAGCACCCGAGTGCTTGCGGAACCGGTG | SEQ ID NO:19 |

| DETECTOR PRIMERS FOR HCV REGION 3 | | |
|---|---|---|
| 3DL1 | TAGCACCCGAGTGCTGCCTGATAGG(T)TGCTTGC | SEQ ID NO:20 |
| 3DL2 | TAGCACCCGAGTGCTGCCTGATAGGG(A)GCTTGC | SEQ ID NO:21 |
| 3DL3 | TAGCACCCGAGTGCTTGCCTGATAGGG(A)GCTTGC | SEQ ID NO:22 |
| 3DR1 | TAGCACCCGAGTGCTGCAAGC(T)CCCTATCAGGC | SEQ ID NO:23 |
| 3DR2 | TAGCACCCGAGTGCTGCAAGC(T)CCCTATCAGGCA | SEQ ID NO:24 |
| 3DR3 | TAGCACCCGAGTGCTCGCAAGC(T)CCCTATCAGGC | SEQ ID NO:25 |
| 3DR4 | TAGCACCCGAGTGCTCGCAAGC(T)CCCTATCAGGCA | SEQ ID NO:26 |
| 3DOL1 | TAGCACCCGAGTGCTGCGAAAG(T)CCTTGTGGTAC | SEQ ID NO:27 |
| 3DOL2 | TAGCACCCGAGTGCTTAGCGAAAG(T)CCTTGTGGTA | SEQ ID NO:28 |
| 3DOL3 | TAGCACCCGAGTGCTGTAGCGAAAG(T)CCTTGTGGTA | SEQ ID NO:29 |
| 3DOL4 | TAGCACCCGAGTGCTGTAGCGAAAG(T)CCTTGTGGT | SEQ ID NO:30 |

(X) = Deliberately mismatched bases

-continued

BUMPER PRIMERS FOR HCV REGION 3

| 3B1.2 | GCGTGC(T)CCCGC(T)AGA | SEQ ID NO:34 |
|---|---|---|
| 3B2.3 | GCACGGTCTACGA | SEQ ID NO:35 |

(X) = Deliberately mismatched bases

The primers and probes set forth above were selected to minimize the effects of heterogeneity in the targeted region of the DNA polymerase gene. Mismatches were confined to the middle or the 5' end of the primers and probes to permit efficient 3' extension upon hybridization to the target sequence.

Because the target binding sequence confers target specificity on the primer or probe, it should be understood that the target binding sequences exemplified above for use as particular components of a specific amplification reaction may also be used in a variety of other ways for detection of HCV. For example, the target binding sequences of SEQ ID NOs:1–30 may alternatively be used as hybridization probes for direct detection of HCV, either without prior amplification or as a post-amplification assay. Such hybridization methods are well known in the art and typically employ a detectable label associated with or linked to the target binding sequence to facilitate detection of hybridization. Further, essentially all of the target binding sequences set forth above may be used as amplification primers in amplification reactions which do not require additional specialized sequences (such as PCR) or appended to the appropriate specialized sequences for use in 3SR, NASBA, transcription-based or any other primer extension amplification reactions. For detection of amplification products, amplification primers comprising the target binding sequences disclosed herein may be labeled as is known in the art, or labeled detector primers comprising the disclosed target binding sequences may be used in conjunction with the amplification primers as described in U.S. Pat. Nos. 5,547,861; 5,928,869; 5,593,867; 5,550,025; 5,935,791; 5,888,739; 5,846,726 for real-time homogeneous detection of amplification. Such detector primers may comprise a directly or indirectly detectable sequence which does not initially hybridize to the target but which facilitates detection of the detector primer once it has hybridized to the target and been extended. For example, such detectable sequences may be sequences which form a secondary structure, sequences which contain a restriction site, or linear sequences which are detected by hybridization of their complements to a labeled oligonucleotide (sometimes referred to as a reporter probe) as is known in the art.

Alternatively, the amplification products may be detected post-amplification by hybridization of a probe selected from any of the target binding sequences disclosed herein which fall between a selected set of amplification primers.

It is to be understood that an oligonucleotide according to the invention which consists of a target binding sequence and, optionally, either a sequence required for a selected amplification reaction or a sequence required for a selected detection reaction may also include certain other sequences which serve as spacers, linkers, sequences for labeling or binding of an enzyme, etc. Such additional sequences are typically known to be necessary to obtain optimum function of the oligonucleotide in the selected reaction and are intended to be included by the term "consisting of."

EXAMPLE

Use of the primers and probes of the invention may be exemplified using an SDA reaction to detect Region 1 of the HCV UTR. For such a reaction one "left" amplification primer is selected from SEQ ID NOs:1–2 and one "right" amplification primer is selected from SEQ ID NOs:3–8. To detect Region 3 of the UTR, one "left" amplification primer is selected from SEQ ID NOs:9–11 and one "right" amplification primer is selected from SEQ ID NOs:12–15. A detector primer is also selected from SEQ ID NOs:16–19 for detection of Region 1 or from SEQ ID NOs:20–30 for detection of Region 3, and the hairpin is labeled with a donor/quencher dye pair as is known in the art for detection of target amplification. Fluorescein and dabcyl are preferred dyes for this purpose. Finally, either SEQ ID NO:31 or SEQ ID NO:32 may be selected as the "left" bumper primer for amplification of Region 1 and SEQ ID NO:33 serves as the "right" bumper primer. SEQ ID NO:34 and SEQ ID NO:35 are the "left" and "right" bumper primers, respectively, for amplification of Region 3. SDA is preferably performed at about 52° C. as described in U.S. Pat. No. 5,648,211 using the selected detector primer to provide detection of the target during amplification as described in U.S. Pat. Nos. 5,919,630; 5,928,869 and 5,958,700.

Donor fluorescence is monitored during the amplification reaction. In the presence of HCV target nucleic acids, donor fluorescence will increase as the hairpin holding the donor and quencher in close proximity is unfolded. In the absence of target, fluorescence will remain consistently low throughout the reaction. An increase in fluorescence or a failure of fluorescence to change substantially indicate the presence or absence of HCV target, respectively. Typically, the generation of a relatively higher amount of fluorescence indicates a higher initial level of target.

What is claimed is:

1. An oligonucleotide having a sequence consisting of the target binding sequence corresponding to any one of SEQ ID NO:20 through SEQ ID NO:29 and, optionally, a sequence required for a selected detection reaction.

2. The oligonucleotide of claim 1 which consists of the target binding sequence corresponding to SEQ ID NO:20 and, optionally, a sequence required for a selected detection reaction.

3. The oligonucleotide of claim 1 which consists of the target binding sequence corresponding to SEQ ID NO:21 and, optionally, as sequence required for a selected detection reaction.

4. The oligonucleotide of claim 1 which consists of the target binding sequence corresponding to SEQ ID NO:22 and, optionally, a sequence required for a selected detection reaction.

5. The oligonucleotide of claim 1 which consists of any one of SEQ ID NO:20 through SEQ ID NO:29.

6. The oligonucleotide of claim 1 wherein the sequence required for the detection reaction is a hairpin, a G-quartet, a restriction site or a sequence which hybridizes to a reporter probe.

7. The oligonucleotide of claim 1 which is labeled with a detectable label.

8. The oligonucleotide of claim 7 wherein the label is a fluorescent label.

9. The oligonucleotide of claim 1 which consists of the target binding sequence corresponding to SEQ ID NO:23 and, optionally, a sequence required for a selected detection reaction.

10. The oligonucleotide of claim 1 which consists of the target binding sequence corresponding to SEQ ID NO:24 and, optionally, a sequence required for a selected detection reaction.

11. The oligonucleotide of claim 1 which consists of the target binding sequence corresponding to SEQ ID NO:25 and, optionally, a sequence required for a selected detection reaction.

12. The oligonucleotide of claim 1 which consists of the target binding sequence corresponding to SEQ ID NO:26 and, optionally, a sequence required for a selected detection reaction.

13. The oligonucleotide of claim 1 which consists of the target binding sequence corresponding to SEQ ID NO:27 and, optionally, a sequence required for a selected detection reaction.

14. The oligonucleotide of claim 1 which consists of the target binding sequence corresponding to SEQ ID NO: 28 and, optionally, a sequence required for a selected detection reaction.

15. The oligonucleotide of claim 1 which consists of the target binding sequence corresponding to SEQ ID NO: 29 and, optionally, a sequence required for a selected detection reaction.

* * * * *